(12) United States Patent
Parsons

(10) Patent No.: US 8,716,017 B2
(45) Date of Patent: May 6, 2014

(54) TECHNOLOGIES, METHODS, AND PRODUCTS OF SMALL MOLECULE DIRECTED TISSUE AND ORGAN REGENERATION FROM HUMAN PLURIPOTENT STEM CELLS

(75) Inventor: Xuejun Huang Parsons, San Diego, CA (US)

(73) Assignee: San Diego Regenerative Medicine Institute, San Diego, CA (US)

( * ) Notice: Subject to any disclaimer, the term of this patent is extended or adjusted under 35 U.S.C. 154(b) by 59 days.

(21) Appl. No.: 13/306,114

(22) Filed: Nov. 29, 2011

(65) Prior Publication Data

US 2012/0301437 A1 Nov. 29, 2012

Related U.S. Application Data

(60) Provisional application No. 61/458,965, filed on Dec. 6, 2010.

(51) Int. Cl.
 *C12N 5/00* (2006.01)

(52) U.S. Cl.
 USPC .......................................................... 435/325

(58) Field of Classification Search
 USPC .......................................................... 435/325
 See application file for complete search history.

(56) References Cited

U.S. PATENT DOCUMENTS

| | | | |
|---|---|---|---|
| 2005/0233446 A1 | 10/2005 | Parsons | |
| 2007/0010011 A1 | 1/2007 | Parsons | |
| 2008/0241919 A1 | 10/2008 | Parsons | |
| 2012/0301437 A1 | 11/2012 | Parsons | |

FOREIGN PATENT DOCUMENTS

| WO | WO/2005/065354 | | 7/2005 |
|---|---|---|---|
| WO | WO2005/065354 | * | 7/2005 |
| WO | WO/2012/078470 | | 6/2012 |

OTHER PUBLICATIONS

Perlmann et al (Genes Dev, 9(7): 769-82, 1995).*
Parsons XH, Teng YD, Moore DA, Snyder EY. Patents on technologies of human tissue and organ regeneration from pluripotent human embryonic stem cells (hESCs). Recent Patents on Regenerative Medicine 2011;1:142-163. PMID: 2335596. PMC3554241.
Parsons XH, Teng YD, Parsons JF, Snyder EY, Smotrich DB, Moore DA. Efficient derivation of human neuronal progenitors and neurons from pluripotent human embryonic stem cells with small molecule induction. Journal of Visualized Experiments 2011;56:e3273. DOI: 10.3791/3273. PMID: 22064669. PMC3227216.
Parsons XH. The dynamics of global chromatin remodeling are pivotal for tracking the normal pluripotency of human embryonic stem cells. Anatomy and Physiology 2012:S3:002. DOI: 10.4172/2161-0940.S3-002. PMID: 23543848. PMC3609651.
Parsons XH. MicroRNA profiling reveals distinct mechanisms governing cardiac and neural lineage-specification of pluripotent human embryonic stem cells. Journal of Stem Cell Research and Therapy 2012;2:124. DOI: 10.4172/2157-7633.1000124. PMID: 23355957. PMC3554249.
Parsons XH. An engraftable human embryonic stem cell neuronal lineage-specific derivative retains embryonic chromatin plasticity for scale-up CNS regeneration. Journal of Regenerative Medicine and Tissue Engineering. 2012;1:3. DOI: 10.7243/2050-1218-1-3. PMID: 23542901. PMC3609668.
Parsons XH, Parsons JF, Moore DA. Genome-scale mapping of microRNA signatures in human embryonic stem cell neurogenesis. Molecular Medicine and Therapeutics 2013;1:2. DOI: 10.4172/2324-8769.1000105. PMID: 23543894. PMC3609664.
Parsons XH. Human stem cell derivatives retain more open epigenomic landscape when derived from pluripotent cells than from tissues. Journal of Regenerative Medicine 2013;1:2. DOI: 10.4172/2325-9620.1000103.
Parsons XH, Teng YD, Parsons JF, Snyder EY, Smotrich DB, Moore DA. Efficient derivation of human cardiac precursors and cardiomyocytes from pluripotent human embryonic stem cells with small molecule induction. Journal of Visualized Experiments 2011;57:e3274, DOI: 10.3791/3274. PMID: 22083019. PMC3308594.
Parsons JF, Smotrich DB, Gonzalez R, Snyder EY, Moore DA, Parsons XH. Defining conditions for sustaining epiblast pluripotence enables direct induction of clinically-suitable human myocardial grafts from biologics-free human embryonic stem cells. Journal of Clinical and Experimental Cardiology 2012;S9:001. DOI: 10.4172/2155-9880.S9-001. PMID: 22905333. PMC3419496.
Parsons XH. Embedding the future of regenerative medicine into the open epigenomic landscape of pluripotent human embryonic stem cells. Annual Review and Research in Biology 2013;3(4):323-349.

* cited by examiner

*Primary Examiner* — Marcia S Noble
*Assistant Examiner* — Magdalene Sgagias

(57) ABSTRACT

Pluripotent human embryonic stem cells (hESCs) hold great potential for restoring tissue and organ function, which has been hindered by inefficiency and instability of generating desired cell types through multi-lineage differentiation. This instant invention is based on the discovery that pluripotent hESCs maintained under defined culture conditions can be uniformly converted into a specific lineage by small molecule induction. Retinoic acid induces specification of neuroectoderm direct from the pluripotent state of hESCs and triggers progression to neuronal progenitors and neurons efficiently. Similarly, nicotinamide induces specification of cardiomesoderm direct from the pluripotent state of hESCs and triggers progression to cardiac precursors and cardiomyocytes efficiently. This technology provides a large supply of clinically-suitable human neuronal or cardiac therapeutic products for CNS or myocardium repair. This invention enables well-controlled efficient induction of pluripotent hESCs exclusively to a specific clinically-relevant lineage for tissue and organ engineering and regeneration, cell-based therapy, and drug discovery.

9 Claims, 11 Drawing Sheets

Lineage-Specific Differentiation of Pluripotent Cells by Small Molecule Induction a.

b.

TECHNOLOGIES, METHODS, AND PRODUCTS OF SMALL MOLECULE DIRECTED TISSUE AND ORGAN REGENERATION FROM HUMAN PLURIPOTENT STEM CELLS

GOVERNMENT INTEREST

This invention was made with government support under Grant No. AG024496 and HD056530 awarded by the National Institutes of Health. The government has certain rights in this invention.

PARENT CASE TEXT

CROSS REFERENCES TO RELATED APPLICATIONS

This application claims priority to U.S. provisional patent application No. U.S. 61/458,965, filed Dec. 6, 2010. The priority application is hereby incorporated herein by reference in its entirety.

REFERENCES CITED

1. Parsons X H, Teng Y D, Moore D A, Snyder E Y. (2011) Patents on technologies of human tissue and organ regeneration from pluripotent human embryonic stem cells. Recent Patents on Regenerative Medicine 1:142-163. PMID: 2335596. PMC3554241.
2. Parsons X H. (2013) Embedding the future of regenerative medicine into the open epigenomic landscape of pluripotent human embryonic stem cells. Ann. Rev. Res. Biol. 3(4):323-349.
3. Redmond D E Jr, et al. (2007) Behavioral improvement in a primate Parkinson's model is associated with multiple homeostatic effects of human neural stem cells. Proc Natl Acad Sci USA 104:12175-12180.
4. Parsons X H, Teng Y D, Parsons J F, Snyder E Y, Smotrich D B, Moore D A. (2011) Efficient derivation of human cardiac precursors and cardiomyocytes from pluripotent human embryonic stem cells with small molecule induction. JoVE 57:e3274. DOI: 10.3791/3274. PMID: 22083019. PMC3308594.
5. Parsons J F, Smotrich D B, Gonzalez R, Snyder E Y, Moore D A, Parsons X H. (2012) Defining conditions for sustaining epiblast pluripotence enables direct induction of clinically-suitable human myocardial grafts from biologics-free hESCs. J. Clinic. Exp. Cardiology S9:001. DOI: 10.4172/2155-9880.S9-001. PMID: 22905333. PMC3419496.
6. Parsons X H. (2012) The dynamics of global chromatin remodeling are pivotal for tracking the normal pluripotency of human embryonic stem cells. Anatom. Physiol. S3:002. DOI: 10.4172/2161-0940.S3-002. PMID: 23543848. PMC3609651.
7. Parsons X H, Teng Y D, Parsons J F, Snyder E Y, Smotrich D B, Moore D A. (2011) Efficient derivation of human neuronal progenitors and neurons from pluripotent human embryonic stem cells with small molecule induction. JoVE 56:e3273. DOI: 10.3791/3273. PMID: 22064669. PMC3227216.
8. Parsons X H. (2012) MicroRNA profiling reveals distinct mechanisms governing cardiac and neural lineage-specification of pluripotent human embryonic stem cells. J. Stem Cell Res. Ther. 2:124. DOI: 10.4172/2157-7633.1000124. PMID: 23355957. PMC3554249.
9. Parsons X H. (2012) An engraftable human embryonic stem cell neuronal lineage-specific derivative retains embryonic chromatin plasticity for scale-up CNS regeneration. J. Reg. Med. & Tissue Eng. 1:3. DOI: 10.7243/2050-1218-1-3. PMID: 23542901. PMC3609668.
10. Parsons X H, Parsons J F, Moore D A. (2013) Genome-scale mapping of microRNA signatures in human embryonic stem cell neurogenesis. Mol. Med. Ther. 1:2. DOI: 10.4172/2324-8769.1000105. PMID: 23543894. PMC3609664.
11. Parsons X H. (2013) Human stem cell derivatives retain more open epigenomic landscape when derived from pluripotent cells than from tissues. J. Regen. Med. 1:2. DOI: 10.4172/2325-9620.1000103.

DESCRIPTION

Incorporation by Reference

This application claims benefit of and priority to U.S. provisional patent application Ser. No. U.S. 61/458,965, filed Dec. 6, 2010, which is hereby incorporated by reference as if fully set forth.

FIELD OF THE INVENTION

The present invention relates generally to the fields of human embryonic stem cell biology and regenerative medicine. Specifically, this invention provides technologies, methods and products for well-controlled efficient direct induction of human pluripotent stem cells exclusively to a specific neural or cardiac lineage using small molecules for use in research, drug screening, tissue and organ engineering, tissue and organ regeneration, cell-based therapy, and clinics.

BACKGROUND OF THE INVENTION

Human embryonic stem cells (hESCs) have the unconstrained capacity for long-term stable undifferentiated growth in culture and the intrinsic potential for differentiation into all somatic cell types in the human body [1, 2]. Derivation of hESCs, essentially the in vitro representation of the pluripotent inner cell mass (ICM) or epiblast of the human blastocyst, provides not only a powerful in vitro model system for understanding the human embryonic development, but also a pluripotent reservoir for in vitro derivation of a large supply of disease-targeted human somatic cells that are restricted to the lineage in need of repair [1, 2]. However, how to channel the wide differentiation potential of human pluripotent cells efficiently and predictably to a desired phenotype has been a major challenge for both developmental study and clinical translation. Conventional approaches rely on multi-lineage inclination of pluripotent cells through spontaneous germ layer differentiation, which yields mixed populations of cell types that may reside in three embryonic germ layers and often makes desired differentiation not only inefficient, but uncontrollable and unreliable as well [1, 2]. Although such cells can differentiate spontaneously in vitro into cells of all germ layers by going through a multi-lineage aggregate or embryoid body stage, only a small fraction of cells pursue a given lineage. In those hESC-derived multi-lineage aggregates or embryoid bodies, the simultaneous appearance of a substantial amount of widely divergent undesired cell types that may reside in three embryonic germ layers often makes the emergence of desired phenotypes not only inefficient, but uncontrollable and unreliable as well. Following transplantation, these pluripotent-cell-derived grafts tend to display not only a low efficiency in generating the desired cell types necessary for reconstruction of the damaged structure, but also phenotypic heterogeneity and instability, hence, a high risk of tumorigenicity [1, 2]. Currently, the first-generation of hESC-derived cellular products contains variable levels of mixed populations of cell types, including residual undifferentiated hESCs and partially differentiated cells that retain the capacity to proliferate and differentiate into unwanted cells, raising a potential safety concern. In view of growing interest in the use of human pluripotent cells, including artificially-reprogrammed human induced pluripotent stem cells (hiPS cells) from non-embryonic or adult cell sources, teratoma formation and the emergence of inappropriate cell types have become a constant concern following transplantation [1, 2]. Without a practical strategy to convert pluripotent cells direct into a specific lineage, previous studies and profiling of pluripotent hESCs and their differentiating multi-lineage aggregates have provided little implications to molecular controls in human embryonic development. Developing a novel practical approach that permits to channel the wide differentiation potential of human pluripotent cells efficiently and predictably to a desired phenotype is not only vital to harnessing the power of hESC biology for safe and effective cell-based therapies, but also crucial for unveiling the molecular and cellular cues that direct human embryogenesis.

The hESC lines initially were derived and maintained in co-culture with growth-arrested mouse embryonic fibroblasts (MEFs) [1]. Although several human feeder, feeder-free, and chemically-formulated culture systems have been developed for hESCs, the elements necessary and sufficient for sustaining the self-renewal of human pluripotent cells remain unsolved [1]. These exogenous feeder cells and biological reagents help maintain the long-term stable growth of undifferentiated hESCs whereas mask the ability of pluripotent cells to respond to developmental signals. Therefore, a defined culture system for maintenance of hESCs might not only render specification of clinically-relevant early lineages directly from the pluripotent state without an intervening multi-lineage germ-layer or embryoid body stage, but also allow identify the signaling molecules necessary and sufficient for inducing the cascade of organogenesis in a process that may emulate the human embryonic development [1].

Current therapeutic approaches for a wide range of neurological diseases and injuries provide symptomatic relief but none of them change the prognosis of disease. Therefore, there is a large unfulfilled need for cell-based therapies to provide regeneration and replacement options to restore the lost nerve tissue and function. However, to date, lacking of a clinically-suitable source of engraftable human stem/progenitor cells with adequate neurogenic potential has been the major setback in developing safe and effective cell-based therapies for restoring the damaged or lost central nervous system (CNS) structure and circuitry in a wide range of neurological disorders. The traditional sources of engraftable human stem cells with neural potential for transplantation therapies have been multipotent human neural stem cells (hNSCs) isolated directly from the CNS [3]. These CNS-derived primary hNSCs are neuroepithelial-like cells that are positive for nestin and can spontaneously differentiate into a mixed population of cells containing undifferentiated hNSCs, neurons, astrocytes, and oligodendrocytes in vitro and in vivo [3]. However, cell therapy based on CNS tissue-derived hNSCs has encountered supply restriction and difficulty to use in the clinical setting due to their declining plasticity with aging and limited expansion ability, which makes it difficult to maintain a large scale and prolonged culture and potentially restricts the tissue-derived hNSC as an adequate source for graft material in the clinical setting [3]. Despite some beneficial outcomes, CNS-derived hNSCs appeared to exert their therapeutic effect primarily by their non-neuronal progenies through producing trophic and/or neuroprotective molecules to rescue endogenous dying host neurons [1, 3]. The engrafted tissue-derived stem/progenitor cells generated a small number of neurons that were insufficient to achieve the anticipated mechanism of neuron replacement in the damaged CNS [1, 3].

The genetically stable pluripotent hESCs proffer cures for a wide range of neurological disorders by supplying the diversity of human neuronal cell types in the developing CNS for regeneration and repair. Therefore, they have been regarded as an ideal source to provide an unlimited supply of human neuronal cell types and subtypes for restoring the damaged or lost nerve tissue and function in CNS disorders. However, realizing the developmental and therapeutic potential of hESCs has been hindered by the inefficiency and instability of generating desired cell types from pluripotent cells through multi-lineage differentiation. Although neural lineages appear at a relatively early stage in differentiation, <5% hESCs undergo spontaneous differentiation into neurons [1]. Retinoic acid (RA) does not induce neuronal differentiation of undifferentiated hESCs maintained on feeders [1]. And unlike mouse ESCs, treating hESC-differentiating multi-lineage aggregates—embryoid bodies (EBs)—only slightly increases the low yield of neurons [1, 2]. Under protocols presently employed in the field, these neural grafts derived from pluripotent cells through multi-lineage differentiation yielded neurons at a low prevalence following engraftment, which were not only insufficient for regeneration or reconstruction of the damaged CNS structure, but also accompanied by unacceptably high incidents of teratoma and/or neoplasm formation [1]. Similar to CNS-derived hNSCs, these hESC-derived hNSCs are neuroepithelial-like cells that are positive for nestin and can spontaneously differentiate into a mixed population of cells containing undifferentiated hNSCs, neurons, astrocytes, and oligodendrocytes in vitro and in vivo [1, 2]. Before further differentiation, those secondary hNSCs were mechanically isolated or enriched from hESC-differentiating multi-lineage aggregates or embryoid bodies. Similar to their CNS counterpart, the therapeutic effect of these hESC-derived hNSCs was mediated by neuroprotective or trophic mechanism to rescue dying host neurons, but not related to regeneration from the graft or host remyelination [1, 2]. Growing evidences indicate that these secondary hNSCs derived from hESCs via conventional multi-lineage differentiation in vitro appear to have increased risk of tumorigenicity but not improved neurogenic potential compared to primary hNSCs isolated from the CNS tissue in vivo, remaining insufficient for CNS regeneration [1, 2].

To date, the lack of a suitable human cardiac cell source has been the major setback in regenerating the damaged human myocardium, either by endogenous cells or by cell-based transplantation or cardiac tissue engineering [1, 2]. In the adult heart, the mature contracting cardiac muscle cells (cardiomyocytes) are terminally differentiated and unable to regenerate. Damaged or diseased cardiomyocytes are removed largely by macrophages and replaced by non-functional cells or scar issue. Although cell populations expressing stem/progenitor cell markers have been identified in postnatal hearts, the minuscule quantities and growing evidences indicating that they are not genuine heart cells and that they differentiate predominately to smooth muscle cells rather than functional contractile cardiomyocytes have caused skepticism if they can potentially be harnessed for cardiac repair

[1, 2]. There is no evidence that stem/precursor/progenitor cells derived from other sources, such as mesenchymal stem cells, bone marrow cells, umbilical cord stem cells, cord blood cells, patients' heart tissue, placenta, or fat tissue are able to give rise to the contractile heart muscle cells following transplantation into the heart [1, 2]. Therefore, the need to regenerate or repair the damaged heart muscle (myocardium) has not been met by adult stem cell therapy, either endogenous or via cell delivery, in today's healthcare industry. Pluripotent hESCs proffer unique revenue to generate a large supply of cardiac lineage-committed cells as human myocardial grafts for cell-based therapy. Due to the prevalence of cardiovascular disease worldwide and acute shortage of donor organs or adequate human myocardial grafts, there is intense interest in developing hESC-based therapy for heart disease and failure [1, 2]. The hESCs and their derivatives are considerably less immunogenic than adult tissues [1, 2]. It is also possible to bank large numbers of human leukocyte antigen isotyped hESC lines so as to improve the likelihood of a close match [1, 2].

However, realizing the therapeutic potential of hESCs has been hindered by the inefficiency and instability of generating cardiac cells from pluripotent cells through multi-lineage differentiation. In hESC-differentiating multi-lineage aggregates (embryoid body), only a very small fraction of cells (~1-4%) spontaneously differentiate into cardiomyocytes [1, 2]. Following mechanical isolation and immuno-selection, the small quantity of enriched cardiomyocytes could rescue the function of a damaged myocardium as a biological pacemaker following injection into the heart of animal models [1, 2]. Although such hESC-derived cardiomyocytes can attenuate the progression of heart failure in rodent models of acute myocardial infraction, they are insufficient to restore heart function or to alter adverse remodeling of a chronic myocardial infarction model following transplantation [1, 2].

It can therefore be seen that there is a need to develop new techniques for well-controlled efficiently channeling the wide differentiation potential of pluripotent hESCs exclusively and predictably to a large scale of neuronal lineage committed cells, which is vital to providing a large supply of clinically-suitable human neuronal therapeutic products across the spectrum of developmental stages in high purity and efficiency, and with adequate neurogenic potential for neuronal repair against neurological diseases or injuries.

It can therefore be seen that there is a need to develop new techniques for well-controlled efficiently channeling the wide differentiation potential of pluripotent hESCs exclusively and predictably to a large scale of cardiac lineage committed cells, which is vital to providing a large supply of clinically-suitable human cardiac therapeutic products across the spectrum of developmental stages in high purity and efficiency, and with adequate cardiogenic potential for myocardium repair against cardiovascular diseases.

SUMMARY OF THE INVENTION

The present invention provides the techniques on direct conversion of pluripotent human embryonic stem cells (hESCs) uniformly into a specific clinically-relevant lineage by small molecule induction.

The present invention provides the technique for efficient production of human neuronal progenitors and human neuronal cell types and subtypes in the developing CNS from pluripotent hESCs for neuronal regeneration and replacement therapies against a wide range of neurological disorders.

The present invention provides the technique for efficient production of human cardiac precursors and human cardiomyocytes from pluripotent hESCs for myocardium regeneration and replacement therapies against heart disease and failure.

Accordingly, one embodiment of the invention is provided a method of identifying conditions for well-controlled efficient induction of pluripotent hESCs, maintained under a defined culture system that is capable of insuring the proliferation of undifferentiated hESCs, exclusively to a specific clinically-relevant lineage by small molecule induction.

Another preferred embodiment of the invention is provided a method of lineage-specific differentiation of human pluripotent stem cells to specialized functional cells by small molecule induction.

A particular embodiment of the invention is provided a method of using retinoic acid (RA) to induce the specification of neuroectoderm direct from the pluripotent state of hESCs in a defined culture platform by promoting nuclear translocation of the neuronal-specific transcription factor Nurr-1 and trigger the progression to human neuronal progenitors and human neurons in high efficiency, purity, and neuronal lineage specificity.

Another particular embodiment of the invention is provided a method of using nicotinamide (NAM) to induce the specification of cardiomesoderm direct from the pluripotent state of hESCs in a defined culture platform by promoting the expression of the earliest cardiac-specific transcription factor Csx/Nkx2.5 and trigger the progression to cardiac precursors and beating cardiomyocytes in high efficiency, purity, and cardiac lineage specificity.

These and other embodiments of the invention are further elucidated in the description that follows.

DESCRIPTION OF THE DRAWINGS

Description of the Figures

FIGS. 2-11 represent data from the experiments supporting the invention.

Figure 1:
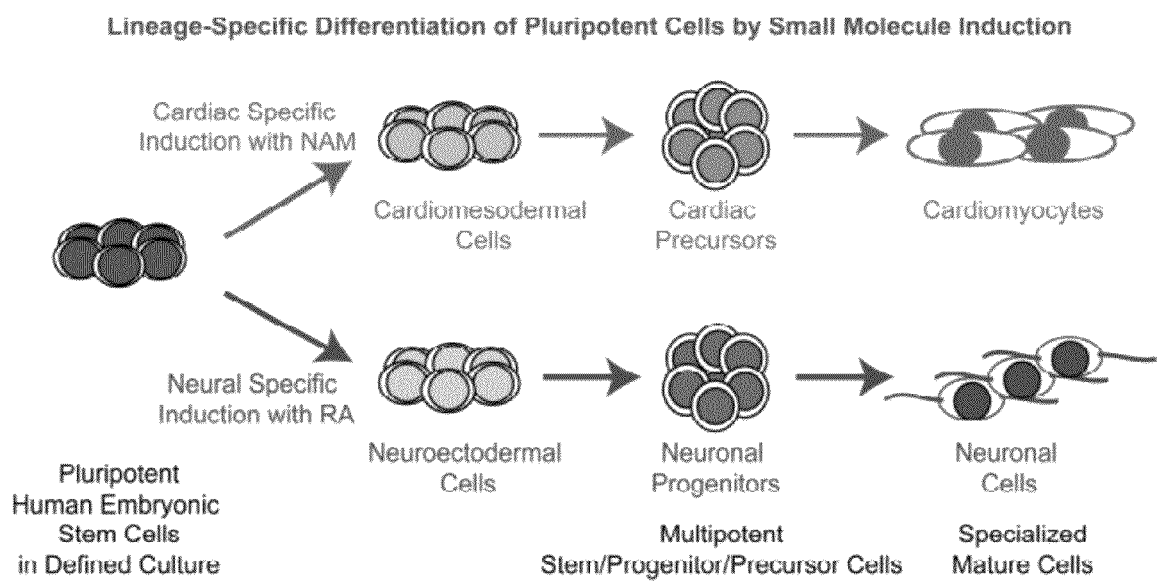

FIG. 1. Overall scheme of the invention of lineage-specific differentiation of human pluripotent stem cells (hESCs) by small molecule induction for high efficient direct conversion of pluripotent hESCs uniformly into a specific clinically-relevant functional lineage. A schematic of well-controlled efficient specification of pluripotent hESCs exclusively to a functional neural or cardiac lineage by small molecule induction.

Figure 2:
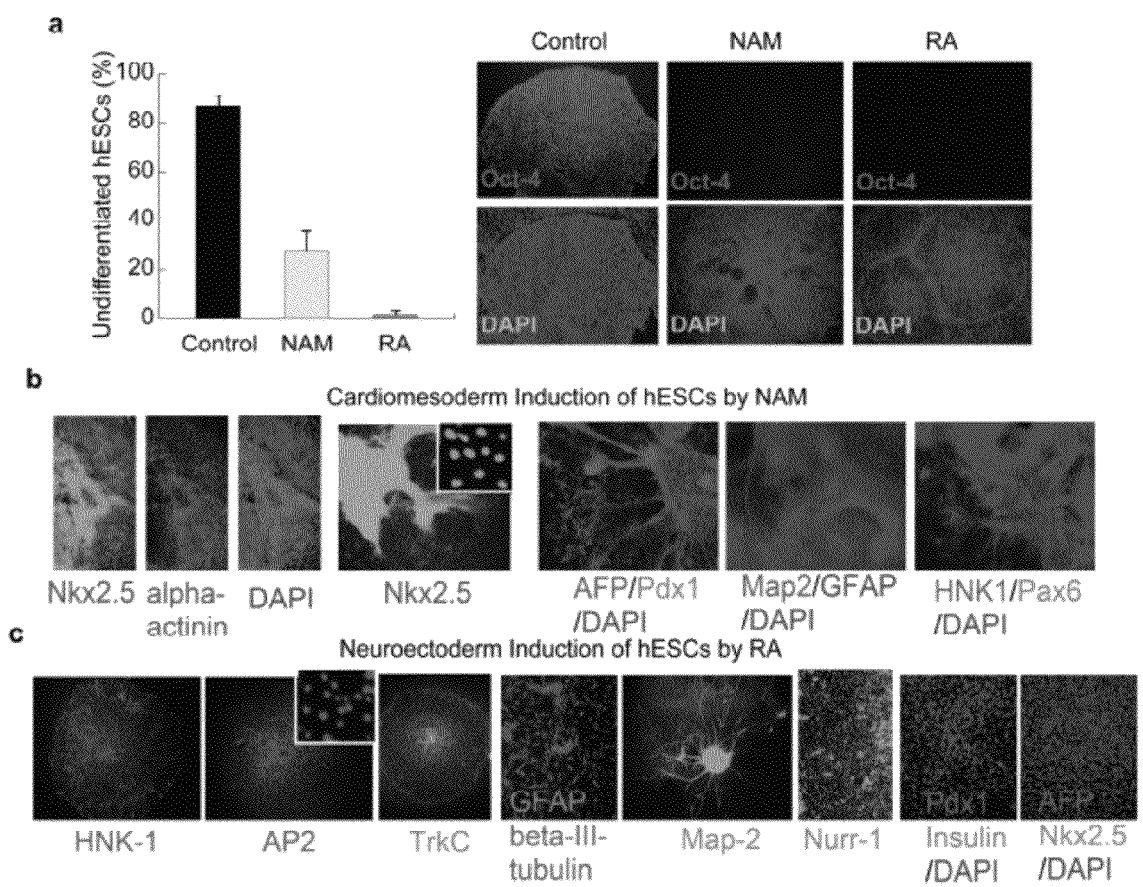

FIG. 2. Small molecules signal cardiac or neural induction direct of pluripotence under defined conditions.
  (a) Upon exposure of undifferentiated hESCs to nicotinamide (NAM) or retinoic acid (RA) under the defined culture system, all the cells within the colony underwent morphology changes to large differentiated cells that down-regulated (with NAM) or ceased (with RA) expressing pluripotence-associated markers, as indicated by Oct-4 (red).
  (b) Cardiac fate switch direct of the pluripotent state of hESCs induced by nicotinamide. NAM-induced Oct-4-negative cells began to express the cardiac specific transcription factor (Csx) Nkx2.5 (green) and alpha-actinin (red), consistent with early cardiac differentiation. Progressively increased intensity of Nkx2.5 was usually observed in areas of the colony where cells began to pile up. These differentiated cells did not express markers for other lineages, including AFP (red), Pdx1 (green) [endoderm], Map-2 (red), GFAP (green), HNK1 (red), and Pax6 (green) [ectoderm]. All cells are indicated by DAPI staining of their nuclei (blue). Insets at the top better visualize individual cells at higher-magnification. These data suggested that NAM was sufficient for inducing the pluripotent hESCs maintained in the defined culture system to transition from a pluripotent state exclusively to a cardiomesodermal phenotype.

(c) Neural fate switch direct of the pluripotent state of hESCs induced by retinoic acid. RA-induced differentiated Oct-4-negative cells began to express HNK1 (red), AP2 (red), TrkC (green), and β-III-tubulin (red), consistent with early neuroectodermal differentiation, but not markers associated with other lineages, including Pdx1 (red), AFP (red), and insulin (green) [endoderm], Nkx2.5 (green) [mesoderm], and GFAP (green) [glial cells]. These differentiated cells continued to multiply and the colonies increased in size, proceeding spontaneously to mature ultimately expressing the neuronal marker Map-2 (green), usually in areas where cells began to pile up. All cells are indicated by DAPI staining of their nuclei (blue). Insets at the top better visualize individual cells at higher-magnification. These data suggested that RA was rendered sufficient to induce hESCs maintained in the defined culture system to transition from a pluripotent state exclusively to a neuroectodermal phenotype.

Figure 3:
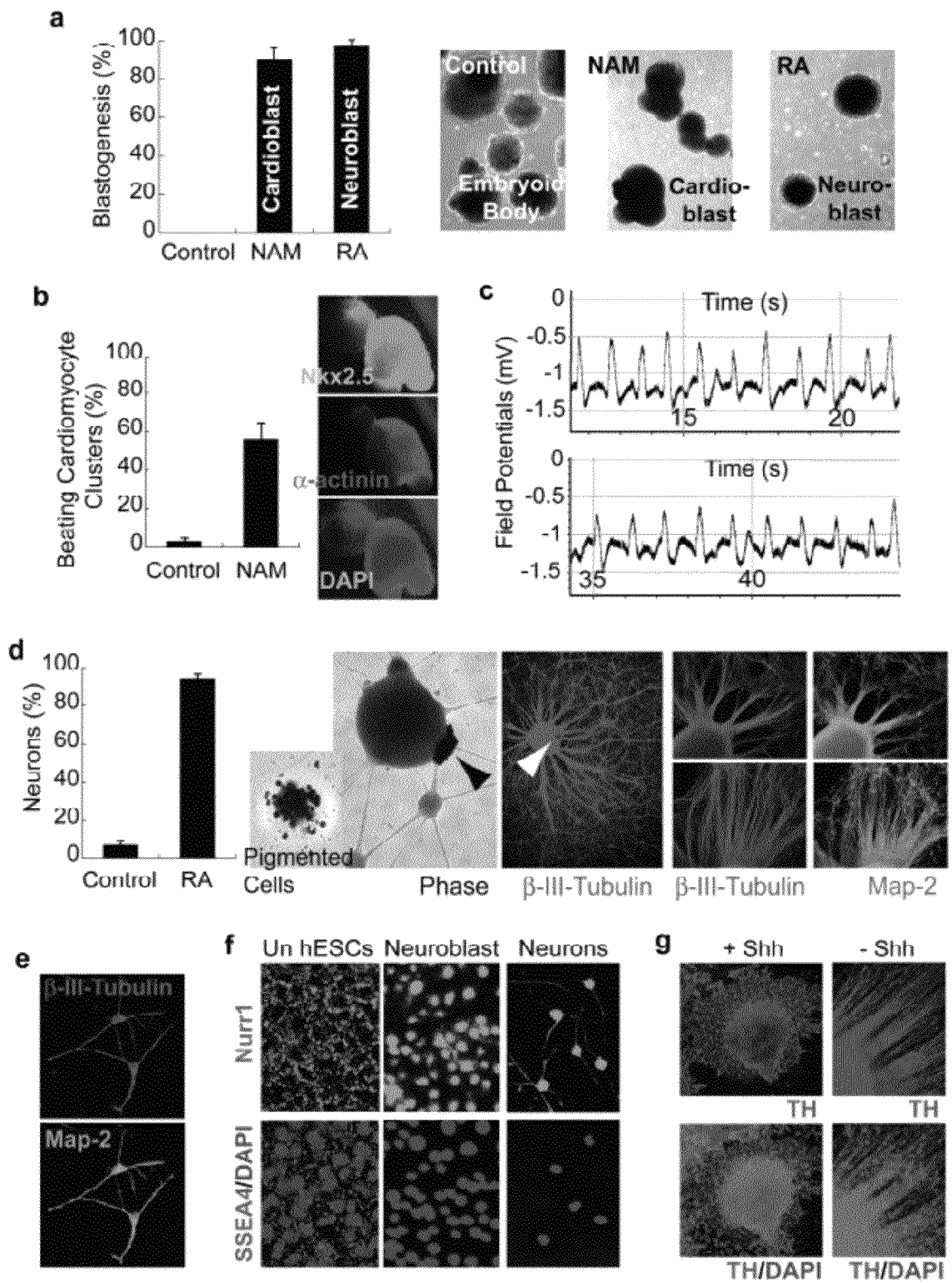

FIG. 3. The cardiac- or neural-induced hESCs capable of progression to beating cardiomyocytes or ventral neurons with high efficiency.

(a) The induced hESCs formed cardioblasts (Nkx2.5+, with NAM) or neuroblasts (β-III-tubulin+, with RA) in suspension, as compared to germ-layer-induced multi-lineage embryoid bodies (EBs) derived from hESCs without treatment (Control) over the same time period.

(b) NAM-induced hESCs yielded beating cardiomyocytes with a drastic increase in efficiency after permitting to attach when compared to those from spontaneous differentiation without treatment (control), as assessed by the percentages of cellular clusters that displayed rhythmic contractions, and immunopositive for markers characteristic of cardiomyocytes, including Nkx2.5 (green) and α-actinin (red) (DAPI is blue).

(c) Electrophysiological profiles of the beating cardiomyocytes confirmed their contractions to be strong, rhythmic, well-coordinated, and well-entrained, with regular impulses reminiscent of the p-QRS-T-complexes seen from body surface electrodes in clinical electrocardiograms (data also recorded in Videos, see reference [4]).

(d) Upon removal of bFGF and after permitting the RA-induced neuroblasts to attach, β-III-tubulin (red) and Map-2- (green) expressing, neurite-bearing cells and pigmented cells (arrow, typical of those in the ventral mesencephalon) began to appear with a drastic increase in efficiency when compared to similarly cultured cells derived from embryoid bodies (EBs) without treatment (control).

(e) Such preparations could also be dissociated with trypsin and maintained as a monolayer wherein the RA-induced cells continued to pursue a neuronal fate as suggested by their β-III-tubulin (red) and Map-2 (green) immunopositivity.

(f) Nurr1 translocates to the nucleus upon exposure of hESCs to RA. Nurr1, a member of the orphan nuclear hormone receptor super-family, has been implicated in neuronal development, particularly ventral mesencephalic development and activation of the tyrosine hydroxylase (TH) gene, the rate-limiting step in catecholaminergic and dopaminergic neuronal differentiation. In undifferentiated hESCs, Nurr1 localizes to the cell-surface and cytoplasm, consistent with its being inactive. However, upon exposure of the hESCs to RA, Nurr1 translocated to the nucleus, coincident with the appearance of the neuroectodermal cells, and continued to assume its strong expression and nuclear localization at the later neuronal stages. All cells are indicated by DAPI staining of their nuclei (blue).

(g) A large subpopulation of these hESC-derived neuronal cells progressed to express tyrosine hydroxylase (TH, red) in the presence Sonic hedgehog (+Shh) or absence Sonic hedgehog (−Shh). Sonic hedgehog (Shh) appeared to promote the proliferation of those ventral neuronal cells. All cells are indicated by DAPI staining of their nuclei (blue).

Figure 4:
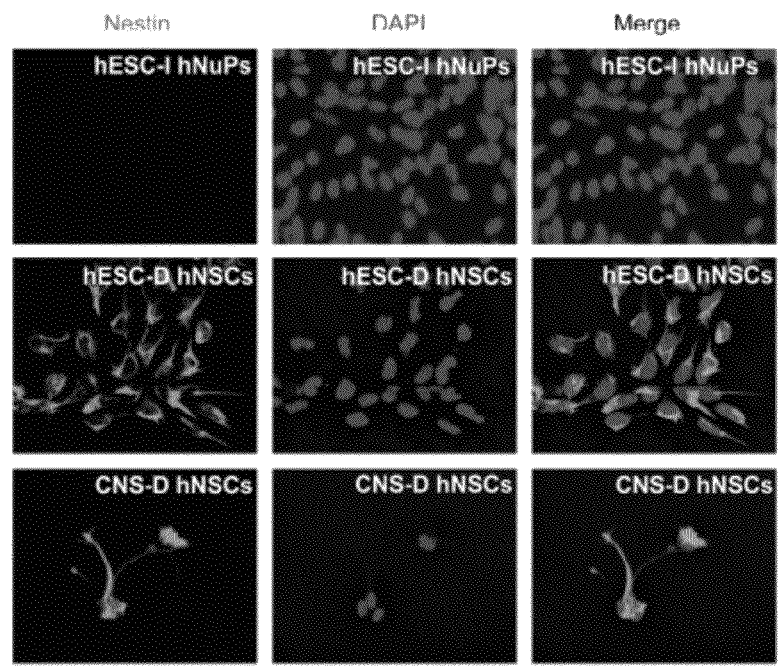
Figure 4:
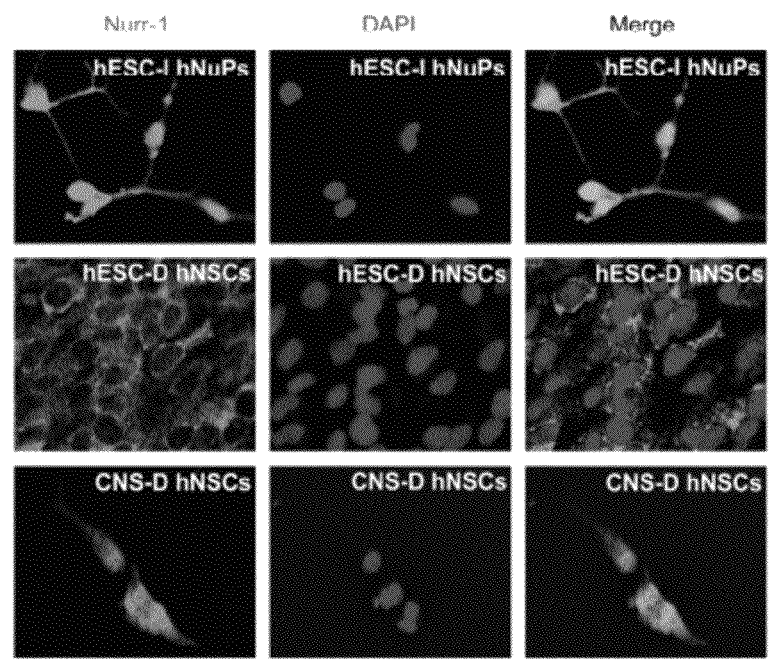

FIG. 4. Comparing Nurr-1 and Nestin expression and cellular localization pattern in neuroectoderm-derived human neuronal progenitors direct from the pluripotent state of hESCs by RA induction (hESC-I hNuPs) to the two prototypical neuroepithelial-like human neural stem cells (hNSCs) either derived from hESCs via conventional multi-lineage differentiation (hESC-D hNSCs) or isolated directly from human fetal CNS (CNS-D hNSCs) as controls.

(a) RA-induced neuroectoderm-derived hESC-I hNuPs do not express Nestin (green), compared to the two prototypical neuroepithelial-like Nestin-positive hNSCs either derived from hESCs or CNS.

(b) RA-induced neuroectoderm-derived hESC-I hNuPs display strong expression and nuclear localization of Nurr-1 (green, suggesting its being active), compared to CNS-D hNSCs that show moderate expression and nuclear localization of Nurr-1 and hESC-D hNSCs that show cell-surface and cytoplasm localization of Nurr-1 (suggesting its being inactive).

Figure 5:
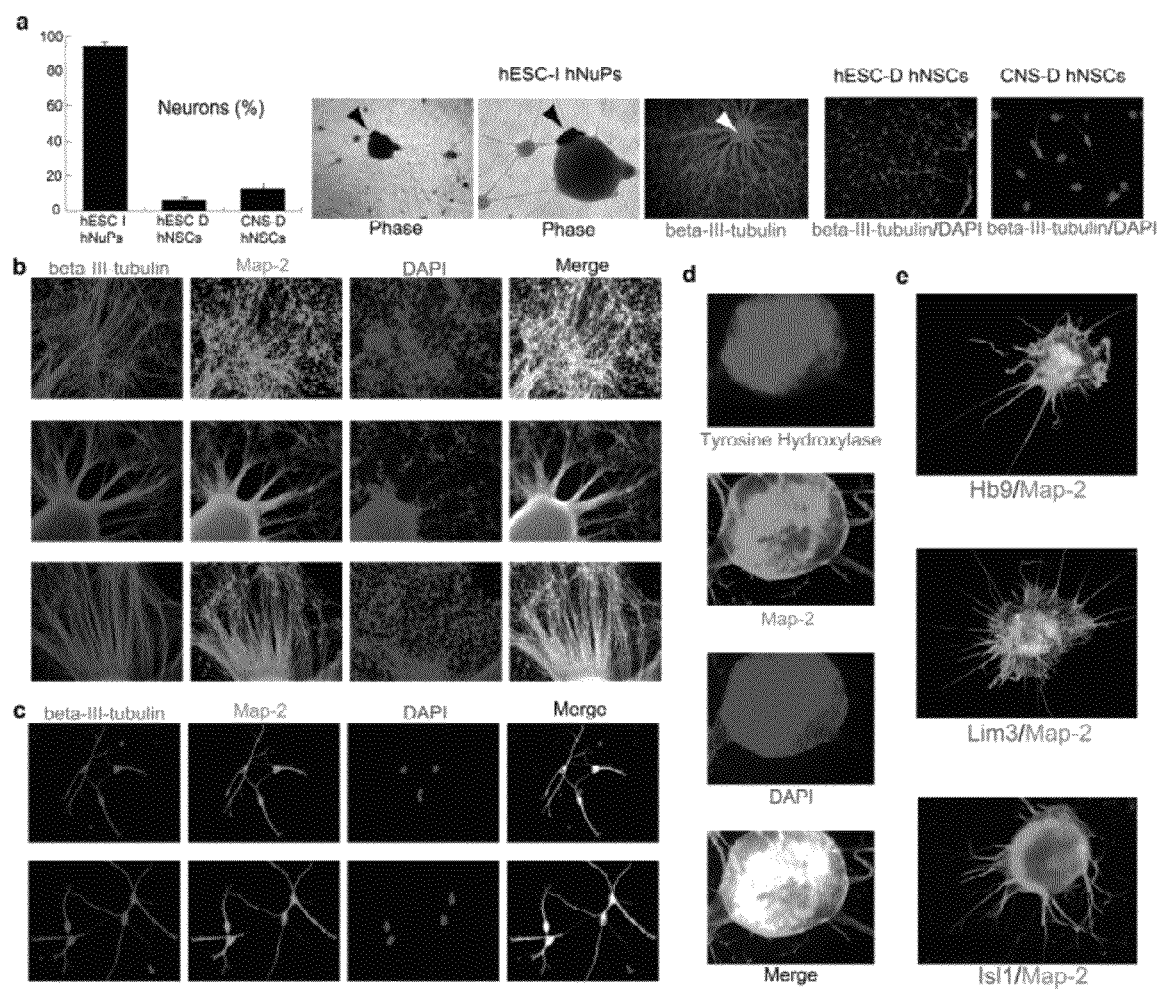

FIG. 5. Neuroectoderm-derived human neuronal progenitors direct from the pluripotent state of hESCs by RA treatment (hESC-I hNuPs) have acquired potent neurogenic ability in vitro.

(a) RA-induced neuroectoderm-derived nuclear Nurr-1-positive hESC-I hNuPs differentiated towards a neuronal lineage with a drastic increase in efficiency (~94%) when compared to the yields of neurons differentiated under similar conditions from the two prototypical neuroepithelial-like Nestin-positive hESC-D hNSCs (~6%) or CNS-D hNSCs (~13%) as controls.

(b) Upon removal of bFGF and after permitting to attach, hESC-I hNuPs yielded exclusively neurons that expressed neuronal marker β-III-tubulin and co-expressed Map-2. No other neural lineages, such as glial cells [e.g., GFAP-positive astrocytes and MBP-positive oligodendrocytes], or non-neural cells were observed. hESC-I hNuPs yielded neurons efficiently and exclusively, as they did not differentiate into glial cells, suggesting that these nuclear Nurr-1 positive hESC-I hNuPs are a novel more lineage-specific neuronal progenitor than the prototypical neuroepithelial-like Nestin-positive hNSCs.

(c) When dissociated and maintained as a monolayer, the RA-induced cells continued to pursue a neuronal fate.

(d, e) Accordingly, a large proportion of these RA-treated hESC-derived neuronal cells began to express markers associated with ventrally-located neuronal populations, such as TH (the tyrosine hydroxylase, marker for dopaminergic [DA] neurons) and Hb9/Lim3/Is11 (markers for motor neurons) (shown in a 3D matrix). All cells are indicated by DAPI staining of their nuclei (blue).

Figure 6:
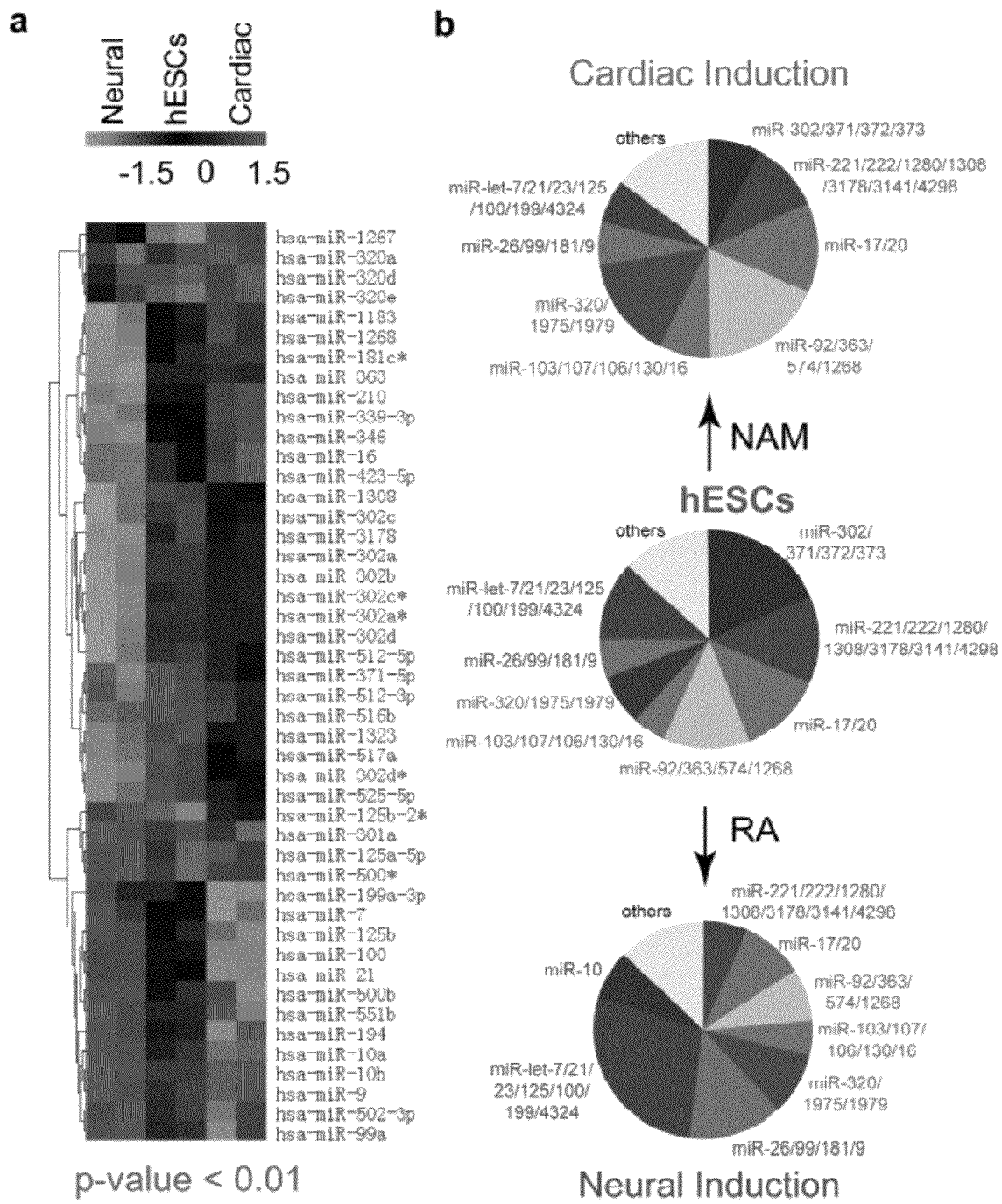

FIG. 6. Genome-scale microRNA (miRNA) profiling of hESC cardiac and neural induction by small molecules.
  (a) Hierarchal clustering of differentially expressed miR-NAs in undifferentiated hESCs (hESC), cardiac-induced hESCs by NAM (Cardiac), and neural-induced hESCs by RA (Neural) by human miRNA microarray analysis.
  (b) Pie charts showing decreased contributions of a set of hESC-associated miRNAs (purple) and increased contributions of distinct sets of cardiac- (green) and neural- (blue) driving miRNAs to the entire miRNA populations upon cardiac (with NAM) and neural (with RA) induction of pluripotent hESCs, including silencing of pluripotence-associated hsa-miR-302 family and a drastic expression increase of neuroectodermal Hox miRNA hsa-miR-10 family upon RA exposure.

Figure 7:
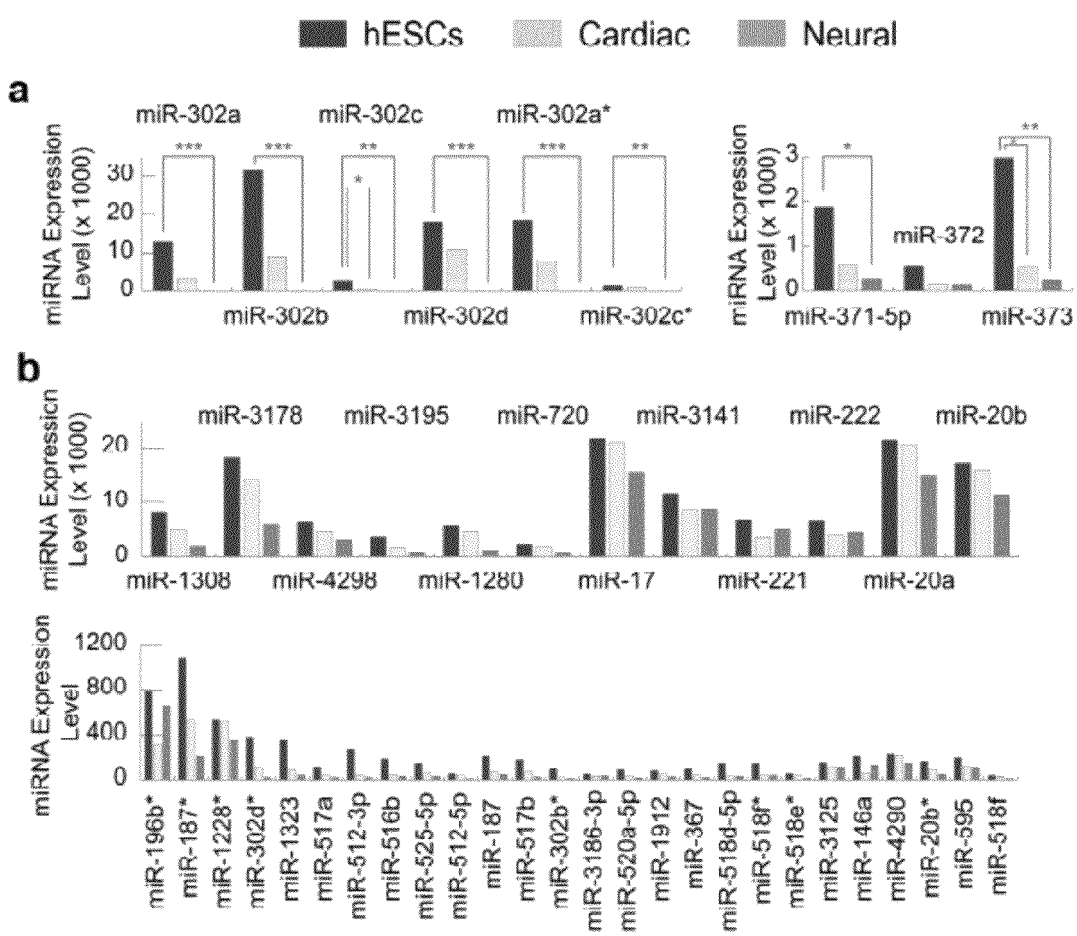

FIG. 7. Down-regulation of a unique set of hESC-associated miRNAs upon lineage induction by small molecules.
  (a) The expression of two most prominent clusters of pluripotence-associated miRNAs hsa-miR-302 and hsa-miR-371/372/373 was significantly suppressed upon lineage-induction of hESCs by small molecules. The cluster of hsa-miR-302 family, which had a profile of the highest expression in pluripotent hESCs, was completely silenced upon neural induction by RA.
  (b) A novel group of abundant miRNA clusters in undifferentiated hESCs, including hsa-miR-1308, 3178, 4298, 3195, 1280, 3141, 221/221, and 720, was found to be significantly down-regulated upon small-molecule-induced lineage differentiation, albeit to less extents. Several clusters of miRNAs that were expressed at low levels but share similar or identical seed sequences with the hsa-miR-302 cluster, including hsa-miR-517, 518, 520, 525, and 367, were also significantly down-regulated upon lineage induction. The clusters of hsa-miR-17 and hsa-miR-20, which were strongly expressed in undifferentiated hESCs and which have near-identical seed sequences with hsa-miR-302 family that have been implicated in cell proliferation, were found to be significantly down-regulated upon RA-induced neural differentiation but not upon NAM-induced cardiac differentiation. In most cases, higher degrees of down-regulation of hESC-associated miRNAs were observed in RA-induced neural differentiation in comparison with NAM-induced cardiac differentiation. *: 5-10 fold, : 10-200 fold, and *: 200-1000 fold of decrease of expression (green lines: cardiac induction by NAM, blue lines: neural induction by RA).

Figure 8:
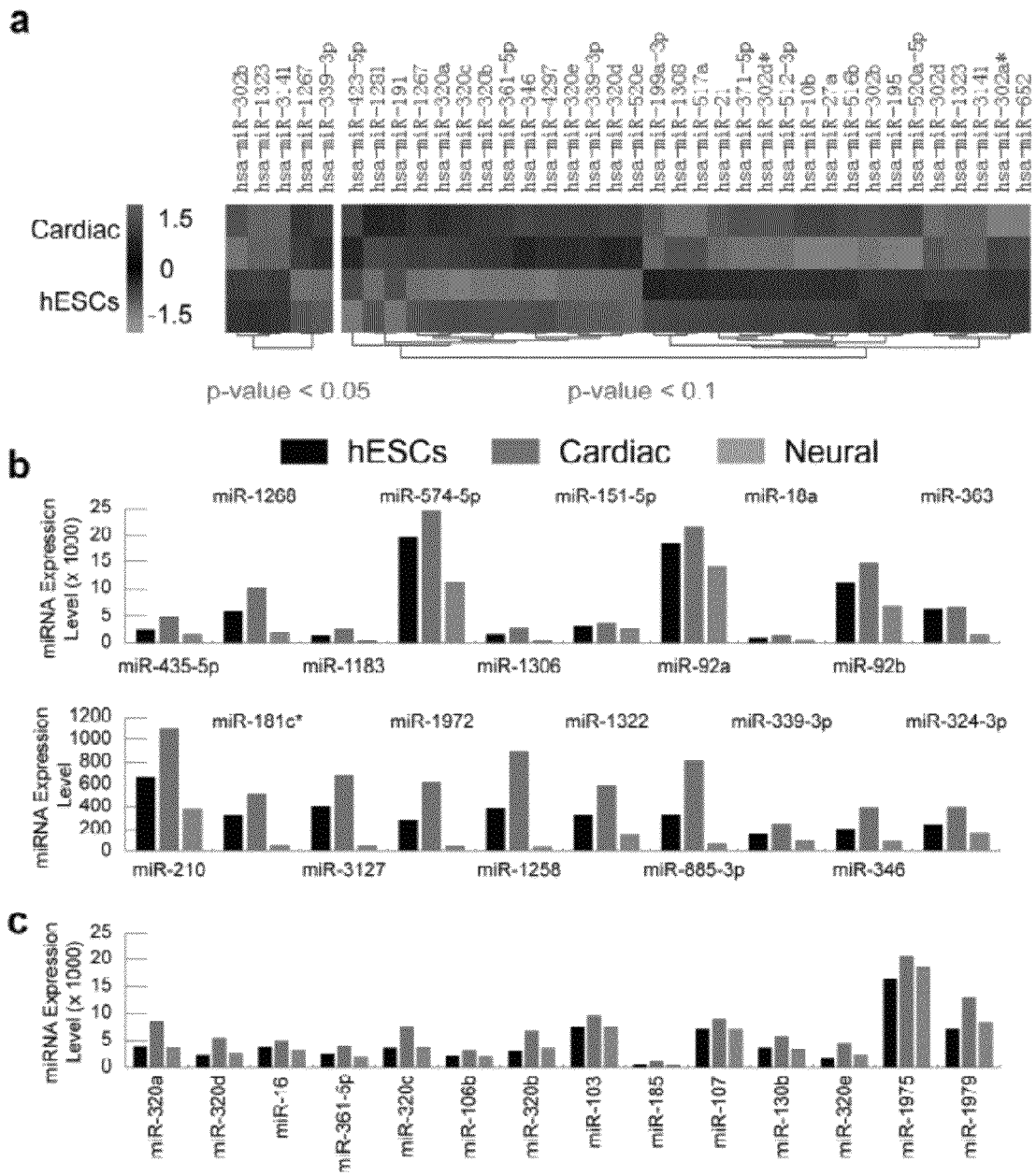

FIG. 8. Up-regulation of a novel set of cardiac-driving miRNAs upon cardiac induction of hESCs by NAM.
  (a) Hierarchal clustering of differentially expressed miRNAs in undifferentiated hESCs (hESC) and cardiac-induced hESCs by NAM (Cardiac).
  (b) A group of cardiac-specific miRNAs displayed an expression pattern of up-regulation upon cardiac induction by NAM and down-regulation upon neural induction by RA. Among this group of cardiac-driving miRNAs, the clusters of hsa-miR-1268, 574-5p, and 92 family contribute to the highest increased expression profile in NAM-induced cardiac differentiation.
  (c) A group of cardiac-specific miRNAs had an expression pattern of up-regulation upon cardiac induction by NAM but was not significantly affected upon neural induction by RA. Among this group of cardiac-driving miRNAs, the clusters of hsa-miR-320 family, 1975, 1979, 103, and 107 contribute to the highest increased expression profile in NAM-induced cardiac differentiation.

These data suggested that a novel set of miRNAs, many of which were not previously linked to cardiac development and function, contributes to initiate the cardiac fate switch of pluripotent hESCs.

Figure 9:
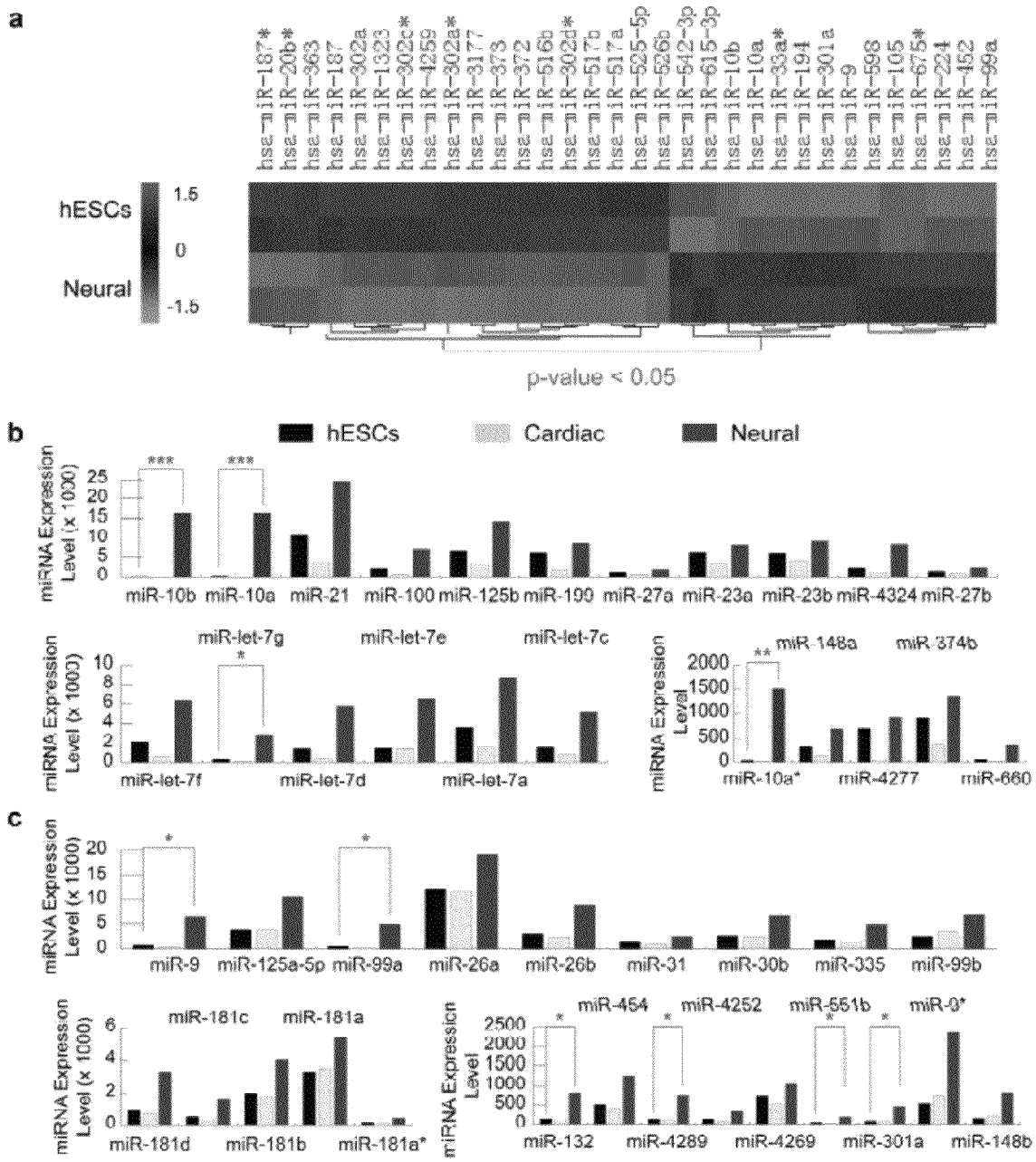

FIG. 9. Up-regulation of a novel set of neural-driving miRNAs upon neural induction by RA.
  (a) Hierarchal clustering of differentially expressed miRNAs in undifferentiated hESCs (hESC) and neural-induced hESCs by RA (Neural).
  (b) A group of neural-specific miRNAs displayed an expression pattern of up-regulation upon neural induction by RA and down-regulation upon cardiac induction by NAM. Among this group of neural-driving miRNAs, the clusters of hsa-miR-10 family, let-7 family (let-7a, c, d, e, f, g), 21, 100, 125b, 23 family, and 4324 contribute to the highest increased expression profile in RA-induced neural differentiation. Notably, the expression of hsa-miR-10 family was silenced in undifferentiated hESCs and displayed a drastic increase (~95-fold) upon RA-induced neural induction. The miR-10 genes locate within the Hox clusters of developmental regulators, and coexpress with a set of Hox genes to repress the translation of Hox transcripts. The drastic expression increase of hsa-miR-10 upon exposure of hESCs to RA suggested that RA might induce the expression of Hox genes and co-expression of Hox miRNA hsa-miR-10 to silence pluripotence-associated genes and miRNA hsa-miR-302 to drive a neural fate switch of pluripotent hESCs, consistent with our observation of a neuroectodermal phenotype of RA-treated hESCs. The let-7 miRNAs silence the ESC self-renewal program in vivo and in culture, down-regulating pluripotence factors such as Myc and Lin28.
  (c) A group of neural-specific miRNAs had an expression pattern of up-regulation upon neural induction by RA but was not significantly affected upon cardiac induction by NAM. Among the this group of neural-driving miRNAs, the clusters of hsa-miR-181 family, 9, 125a-5p, 99 family, 26 family, 30b, and 335 contribute to the highest increased expression profile in RA-induced neural differentiation.

These data suggested that a distinct set of miRNAs, many of which were not previously linked to neural development and function, contributes to initiate the neural fate switch of pluripotent hESCs. * 5-10 fold,  10-50 fold, and * 50-200 fold of increase of expression.

Figure 10:
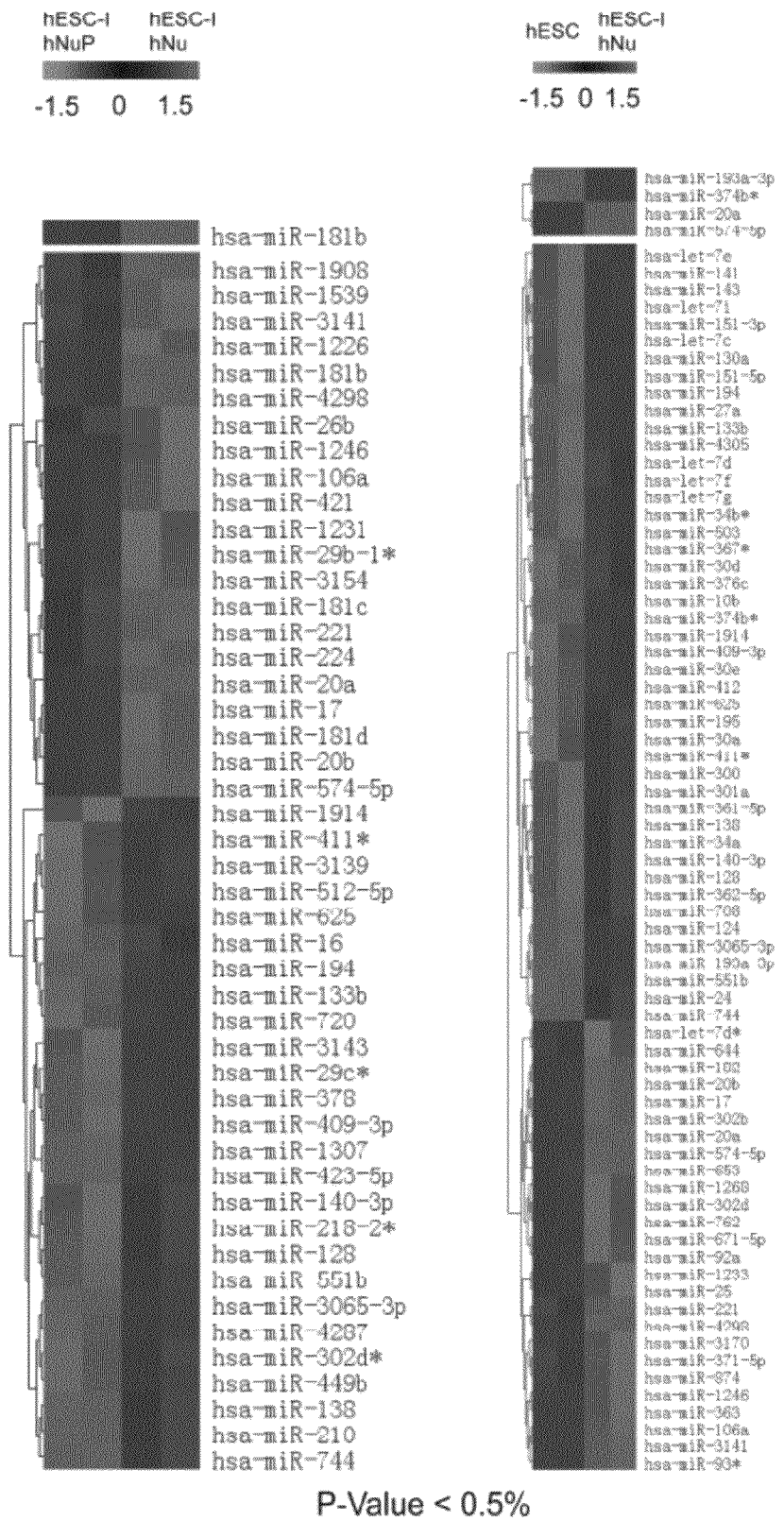

FIG. 10. Genome-scale microRNA (miRNA) profiling of hESC neuronal progression induced by RA. Hierarchal clustering of differentially expressed miRNAs in undifferentiated hESCs (hESC), RA-induced hESC-derived human neuronal progenitors (hESC-I hNuP), and RA-induced hESC-derived human neurons (hESC-I hNu) by human miRNA microarray analysis.

Figure 11:
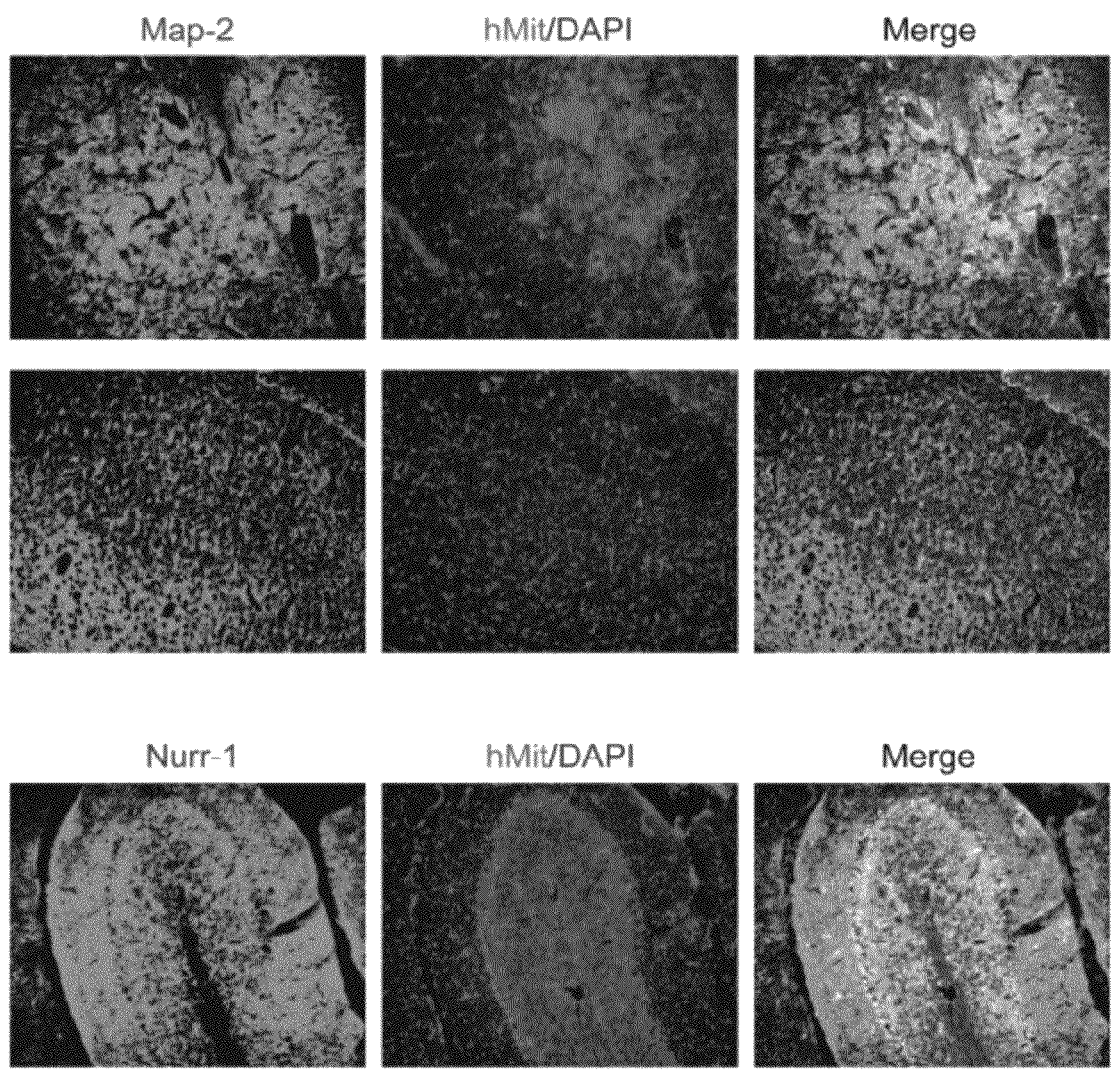

FIG. 11. RA-induced hESC-derived human neuronal progenitors (hESC-I hNuPs) are highly neurogenic in the brain following transplantation. hESC-I hNuPs were injected into the cerebral ventricles of newborn mice affording excellent access to the subventricular zone (SVZ), a secondary germinal zone from which cells widely migrate. Histological analysis of transplanted mice at least 3 months post-grafting showed well-dispersed and well-integrated human neurons exclusively at a high prevalence, indicated by anti-human mitochondrial antibody (hMit) (red) and their immunoreactivity to Map-2 (green), including Nurr1-positve (green) dopaminergic (DA) neurons, within neurogenic regions of the brain. DAPI nuclear marker (blue) stains all cells in the field.

No tumors or non-neuronal cell types were seen. Transplanted mice show hyper activity, such as fast speed movement, fast spin.

DETAILED DESCRIPTION OF THE INVENTION

Pluripotent human embryonic stem cells (hESCs) hold great promise for restoring cell, tissue, and organ function. However, realizing the developmental and therapeutic potential of hESCs has been hindered by the inefficiency and instability of generating desired cell types from pluripotent cells through multi-lineage differentiation. This instant invention is based on the discovery that pluripotent hESCs maintained under the defined culture conditions (i.e., feeder-, serum-, and conditioned-medium-free) can be uniformly converted into a neural lineage or a cardiac lineage by simple provision of small molecules (FIGS. 1-11) [1, 2, 4-11]. In particular, retinoic acid (RA) was identified sufficient to induce the specification of neuroectoderm direct from the pluripotent state of hESCs in a defined platform by promoting nuclear translocation of the neuronal-specific transcription factor Nurr-1 and trigger the progression to human neuronal progenitors and human neurons of the developing CNS in high efficiency, purity, and neuronal lineage specificity [1, 2, 6-11]. Similarly, nicotinamide (NAM) was identified sufficient to induce the specification of cardiomesoderm direct from the pluripotent state of hESCs in a defined platform by promoting the expression of the earliest cardiac-specific transcription factor Csx/Nkx2.5 and trigger the progression to cardiac precursors and beating cardiomyocytes in high efficiency, purity, and cardiac lineage specificity [1, 2, 4-6, 8]. This invention not only provides a large supply of clinical-suitable human neuronal therapeutic products for neuron regeneration and replacement therapy against a wide range of neurological disorders and a large supply of clinical-suitable human cardiac therapeutic products for myocardium regeneration and replacement therapy against heart disease and failure, but also offers means for small-molecule-mediated direct control and modulation of the pluripotent fate of hESCs to a specific lineage when deriving an unlimited supply of clinically-relevant lineages for regenerative medicine.

The hESCs were initially derived and maintained in co-culture with growth-arrested mouse embryonic fibroblasts (MEFs) that compromise the therapeutic potential of these cells because of the risk of transmitting pathogens, altering genetic background, and promoting the expression of immunogenic proteins [1]. Although several human feeder, feeder-free, and artificially-formulated defined culture systems have been suggested for hESCs, the elements for sustaining undifferentiated growth remain unsolved [1]. These exogenous feeder cells and molecules help maintain the long-term growth of undifferentiated hESCs while mask their ability to respond to differentiation inducing signals/molecules. Therefore, previously, I sought to systematically reduce the needs for the growth of undifferentiated hESCs to minimal essential defined components and identified bFGF, insulin, ascorbic acid, and laminin as the minimal essential components for sustaining the epiblast pluripotence of hESCs in a defined culture system, serving as a platform for de novo derivation of clinically-suitable hESCs and effectively directing such hESCs uniformly towards functional lineages with small molecule induction [see US Patent Application Documents US20050233446, US20070010011, US20080241919, and PCT Patent Application Document WO/2005/065354 for inventions by Parsons, Xuejun Huang].

In order to achieve uniformly conversion of pluripotent hESCs to a lineage-specific fate, I have used the defined culture system to screen the differentiation inducing effect of a variety of small molecules and growth factors on the pluripotent state of hESCs [1, 4, 5, 7]. Although neural lineages appear at a relatively early stage in hESC differentiation, treating hESC-differentiated EBs with retinoic acid (RA) only slightly increased the low yield of neurons [1]. RA was not sufficient to induce the neuronal differentiation of undifferentiated hESCs maintained under previously-reported conditions containing feeder cells or feeder-cell-conditioned media [1]. However, I found that such defined conditions rendered small molecule RA sufficient to induce the specification of neuroectoderm direct from the pluripotent state of hESCs that further progressed to human neuronal progenitors and neurons in the developing CNS with high efficiency by promoting nuclear translocation of the neuronal specific transcription factor Nurr1. a member of the orphan nuclear hormone receptor super-family implicated in ventral neuronal development, particularly ventral mesencephalic development and activation of the tyrosine hydroxylase (TH) gene, the rate-limiting step in dopaminergic (DA) neuronal differentiation [1, 7-11] (FIGS. 1-5). Similarly, the defined platform renders NAM sufficient to induce the specification of cardiomesoderm direct from the pluripotent state of hESCs by promoting the expression of the earliest cardiac-specific transcription factor Csx/Nkx2.5 and triggering progression to cardiac precursors and beating cardiomyocytes efficiently [1, 4, 5, 8] (FIGS. 1-3). This compound was not sufficient when applied to hESCs-aggregated embryoid bodies (EBs) or hESCs maintained under previously-reported conditions containing feeder cells or feeder-cell-conditioned media [1, 4, 7]. This instant invention provides a system for a well-controlled efficient approach to specify pluripotent human cells differentiation exclusively to a clinically-relevant lineage by small molecule induction (as illustrated in FIG. 1).

As illustrated in FIG. 1, upon exposure of undifferentiated hESCs maintained in the defined culture to RA (10 μM), all the cells within the colony underwent morphology changes to large differentiated cells that ceased expressing pluripotence-associated markers (e.g., Oct-4) and began expressing neuroectoderm-associated markers (e.g., HNK1, AP2, and TrkC) (Stage 1—Human Neuroectodermal Cells) [1, 7] (FIG. 1; 2a, c). These large differentiated cells continued to multiply and the colonies increased in size, proceeding spontaneously to express the early neuronal marker β-III-tubulin, but not markers associated with other lineages, including Pdx1, AFP, and insulin [endoderm], Nkx2.5 [mesoderm], and GFAP [glial cells] (FIG. 2c). The more mature neuronal marker Map-2 began to appear in areas of the colonies where cells had piled up (FIG. 2c). These differentiating hESCs then formed neuroblasts that uniformly positive for β-III-tubulin in suspension (Stage 2—Human Neuronal Progenitor Cells [hESC-I hNuPs]) [1, 7] (FIGS. 1; 3a). Upon removal of bFGF and after permitting the neuroblasts to attach, β-III-tubulin- and Map-2-expressing, exuberantly neurite-bearing cells and pigmented cells (typical of those in the CNS) began to appear with a drastic increase in efficiency when compared to similarly cultured cells derived from untreated embryoid bodies (EBs) as control (Stage 3—Human Neuronal Cells in the developing CNS) [1, 7] (FIGS. 1; 3d; 5). Such preparations could also be dissociated with trypsin and maintained as a monolayer wherein the RA-induced cells continued to pursue a neuronal fate as suggested by their β-III-tubulin and Map-2 immunopositivity (FIG. 3e) and the absence of markers associated with other neural cells such as glial lineage, as indicated by no cell expressing GFAP and MBP [1, 7]. Nurr1, a member of the orphan nuclear hormone receptor super-family, has been implicated in neuronal development, particularly ventral mesencephalic development and activation of the tyrosine hydroxylase (TH) gene, the rate-limiting step in catecholaminergic and dopaminergic neuronal differentiation. Interestingly, in undifferentiated hESCs, Nurr1 localizes to the cell-surface and cytoplasm, consistent with its being inactive (FIG. 3f). However, upon exposure of the hESCs to RA, Nurr1 translocated to the nucleus, coincident with the appearance of the neuroectodermal cells, and continued to assume its strong expression and nuclear localization at the later process-bearing neuronal stages (FIG. 3f). Accordingly, a large proportion of these hESC-derived neuronal cells began to express TH (FIGS. 3g; 5d), consistent with the early stages of acquiring catecholaminergic or dopaminergic potential. Similarly, a proportion of Map-2+ cells began to express Hb9 and Lim3 (FIG. 5e), markers implicated in the early stages of motor neuron development, another ventrally-located neuronal population. Sonic hedgehog (Shh) appeared to promote the proliferation of those ventral neuronal cells (FIG. 3g).

As illustrated in FIG. 1, upon exposure of undifferentiated hESCs maintained in the defined culture to NAM (10 mM), all the cells within the colony underwent morphology changes to large differentiated cells that down-regulated the expression of pluripotence-associated markers (e.g., Oct-4) and began expressing the earliest marker for heart precursor, Csx/Nkx2.5, but not markers associated with other lineages, including Pdx1 and AFP [endoderm] and Map-2, GFAP, Pax6, and HNK1 [ectoderm] (Stage 1—Human Cardiomesodermal Cells) [1, 4, 5] (FIGS. 1; 2a, b). Increased intensity of Nkx2.5 was usually observed in areas of the colonies where cells began to pile up (FIG. 2b). These differentiating hESCs then formed cardioblasts that uniformly expressed Nkx2.5 in suspension (Stage 2—Human Cardiac Precursor Cells) [1, 4, 5] (FIGS. 1; 3a). After permitting the cardioblasts to attach and further treating them with NAM, beating cardiomyocytes began to appear after withdrawal of NAM with a drastic increase in efficiency (Stage 3—Human Cardiomyocytes and Cardiovascular Cells) [1, 4, 5] (FIGS. 1, 3b). Cells within the beating cardiospheres expressed markers characteristic of cardiomyocytes [1, 4, 5] (FIG. 3b). The cardiomyocytes can retain their strong contractility for over 3 months. Electrical profiles of the cardiomyocytes confirmed their contractions to be strong rhythmic impulses reminiscent of the p-QRS-T-complexes seen from body surface electrodes in clinical electrocardiograms [4] (FIG. 3c). Cardiac specific transcription factor (Csx) Nkx2.5 is an evolutionally conserved homeobox transcription factor indispensable for normal cardiac development. The onset and pattern of early Nkx2.5 expression roughly coincide with the timing and area of cardiac specification, and Nkx2.5 gene continues to be expressed through development in the heart [1]. Expression of Nkx2.5 is the earliest marker for heart precursor cells in all vertebrates so far examined and is essential for proper cardiac septation and formation/maturation of electrical conduction system [1].

Unlike the two prototypical neuroepithelial-like Nestin-positive human neural stem cells (hNSCs) either derived from hESCs or CNS, this novel human neuronal progenitors (hESC-I hNuPs), which have acquired a neuroectodermal identity through RA induction of pluripotent hESCs in vitro [1, 7], do not express Nestin, but assume uniformly strong expression and nuclear localization of Nurr-1 [9] (FIGS. 3f; 4). Although CNS-D hNSCs, which have acquired their neurectodermal identity through in vivo developmental processes, show moderate expression and nuclear localization of Nurr-1, in hESC-D hNSCs, Nurr1 localizes to the cell-surface and cytoplasm, suggesting its being inactive [9] (FIG. 4). Upon removal of bFGF and after permitting to attach, hESC-I hNuPs yielded exclusively neurons that expressed neuronal marker β-III-tubulin and co-expressed Map-2 with a drastic increase in efficiency (~94%) when compared to the yields of β-III-tubulin-positive neurons differentiated under similar conditions from hESC-D hNSCs (~6%) or CNS-D hNSCs (~13%) [9] (FIG. 5a, b). No other neural lineages, such as glial cells [e.g., GFAP-positive astrocytes and MBP-positive oligodendrocytes], or non-neural cells were observed [1, 7]. Such neuronal cell preparations could also be dissociated with trypsin and maintained as a monolayer (FIGS. 3e; 5c). Accordingly, a large proportion of these hESC-derived neuronal cells began to express markers associated with ventrally-located neuronal populations, such as TH (DA neurons) and Hb9/Lim3/Is11 (motor neurons) [1, 7, 9] (FIGS. 3g; 5d, e).

Under protocols presently employed in the field, hESC-derived cellular products consist of a heterogeneous population of mixed cell types, including fully differentiated cells, high levels of various degrees of partially differentiated or uncommitted cells, and low levels of undifferentiated hESCs, posing a constant safety concern when administered to humans. In contrast, hESC-I hNuPs consist of a homogeneous population of human neuronal progenitor cells with potential to yield high levels of neuronal cells (~94%). Accessory cells (e.g., other neural cells) and inappropriate cells (e.g., undifferentiated hESCs, cytotoxic cells, and non-neural cells) are undetectable in the novel hESC-derived cellular product. hESC-I hNuPs yielded neurons efficiently and exclusively, as they did not differentiate into glial cells, suggesting that these Nurr-1 positive hESC-I hNuPs are a novel more lineage-specific neuronal progenitor than the prototypical neuroepithelial-like Nestin positive hNSCs. The small molecule direct induction protocol yields nuclear Nurr-1 positive human neuronal progenitors and neurons of the developing CNS direct form the pluripotent state of hESCs in high efficiency, purity, and neuronal-lineage specificity, therefore, may minimize the risks of teratoma and ectopic tissue formation by eliminating the presence of undifferentiated hESCs and non-neural inappropriate cell types. This invention will dramatically increase the clinical efficacy for graft-dependent neuron replacement/regeneration and safety of hESC-derived cellular products for CNS repair. Similarly, the small molecule direct induction protocol yields human cardiac precursors and cardiomyocytes in high efficiency, purity, and cardiac-lineage specificity, therefore, may minimize the risks of teratoma and ectopic tissue formation by eliminating the presence of undifferentiated hESCs and non-cardiac inappropriate cell types. This invention will dramatically increase the clinical efficacy for graft-dependent myocardium replacement/regeneration and safety of hESC-derived cellular products for cardiovascular repair.

MicroRNAs (miRNAs) are emerging as important regulators of stem cell pluripotence and differentiation [8, 10]. MiRNAs are small, evolutionarily conserved non-coding RNAs that modulate gene expression by inhibiting mRNA translation and promoting mRNA degradation. MiRNAs act as the governors of gene expression networks, thereby modify complex cellular phenotypes in development or disorders. miRNA microarray profile analysis showed that the expression of two most prominent clusters of pluripotence-associated miRNAs hsa-miR-302 family and hsa-miR-371/372/373 was drastically down-regulated upon lineage induction by small molecules [8, 10] (FIGS. 6; 7a; 10). The cluster of hsa-miR-302 family, which had a profile of the highest expression in pluripotent hESCs, was completely silenced in hESC-I hNuPs (average ~550-fold of decrease) [8, 10] (FIGS. 6; 7a; 10), suggesting that hESC-I hNuPs, unlike previous hESC-derived cellular products through multi-lineage differentiation, do not contain any residual pluripotent cells. A novel group of abundant miRNA clusters in pluripotent hESCs, including hsa-miR-17, 20, 221/222, 1280, 1308, 3178, 3141, and 4298, was found to be significantly down-regulated in hESC-I hNuPs, albeit to a less extent [8, 10] (FIG. 6; 7b; 10). The sensitivity, specificity, robustness, and precision of assays to characterize hESC-derived cellular products by employing genomic miRNA profiling are sufficient to provide a reasonable assurance of homogeneity and identity of hESC-derived cellular products, therefore, safety and efficacy when administered to humans.

A group of miRNAs displayed an expression pattern of up-regulation upon neural induction by RA and down-regulation upon cardiac induction by NAM [8] (FIGS. 6; 9a, b). Among the first group of neural-driving miRNAs (neural-specific miRNA group 1), the clusters of hsa-miR-10 family, let-7 family (let-7a, c, d, e, f, g), 21, 100, 125b, 23 family, and 4324 contribute to the highest increased expression profile in RA-induced neural differentiation [8] (FIGS. 6; 9b). Notably, the expression of hsa-miR-10 family was silenced in undifferentiated hESCs and displayed a drastic increase (average ~95-fold) in neuroectoderm-induced hESC-I hNuPs [8, 10] (FIGS. 6; 9; 10). The miR-10 genes locate within the Hox clusters of developmental regulators and coexpressed with a set of Hox genes to repress the translation of Hox transcripts [8]. The enhancer of the mouse Hoxb-1 gene, which controls the RA response and regulates gene expression predominantly in neuroectoderm, contains a retinoic acid response element (RARE) that is not only involved in the ectopic response to RA, but is also essential for establishing the early Hoxb-1 expression pattern in embryonic development [8]. The drastic expression increase of hsa-miR-10 in hESC-I hNuPs suggested that RA might induce the expression of Hox genes and co-expression of Hox miRNA hsa-miR-10 to silence pluripotence-associated genes and hsa-miR-302 to drive a neuroectodermal phenotype and a neuronal fate in hESC-I hNuPs [8, 10]. The let-7 miRNAs down-regulate pluripotence-associated genes such as myc and lin28 [8, 10]. These data suggested that hESC-I hNuPs have acquired a neuronal identity by silencing pluripotence-associated miRNAs and inducing high levels of expression of miRNAs linked to regulating neuronal development and function, consistent with their high neurogenic ability. A second group of miRNAs had an expression pattern of up-regulation upon neural induction but was not significantly affected upon cardiac induction [8] (FIGS. 6; 9a, c). Among the second group of neural-driving miRNAs, the clusters of hsa-miR-181 family, 9, 125a-5p, 99 family, 26 family, 30b, and 335 contribute to the highest increased expression profile in RA-induced neural differentiation [8] (FIGS. 6; 9c). These data suggested that a distinct set of miRNAs, many of which were not previously linked to neural development and function, contribute to initiate the neural fate switch and neuronal progression of pluripotent hESCs [8, 10] (FIGS. 6; 9; 10).

A group of miRNAs displayed an expression pattern of up-regulation upon cardiac induction by NAM and down-regulation upon neural induction by RA [8] (FIGS. 6; 8a, b). Among the first group of cardiac-driving miRNAs, the clusters of hsa-miR-1268, 574-5p, and 92 family contribute to the highest increased expression profile in NAM-induced cardiac differentiation [8] (FIGS. 6; 8b). A second group of miRNAs had an expression pattern of up-regulation upon cardiac induction but was not significantly affected upon neural induction [8] (FIGS. 6; 8a, c). Among the second group of cardiac-driving miRNAs, the clusters of hsa-miR-320 family, 1975, 1979, 103, and 107 contribute to the highest increased expression profile in NAM-induced cardiac differentiation [8] (FIGS. 6; 8c). These data suggested that a novel set of miRNAs, many of which were not previously linked to cardiac development and function, contribute to initiate the cardiac fate switch and cardiac progression of pluripotent hESCs [8] (FIGS. 6; 8).

The analysis of genome-scale miRNA profiling identified novel sets of development-initiating small molecule miRNAs upon small-molecule-induced cardiac- and neural-specification of hESCs [8] (FIGS. 6-10). A unique set of pluripotence-associated miRNAs was down-regulated, while novel sets of distinct cardiac- and neural-driving miRNAs were up-regulated upon small-molecule-induced lineage-specific differentiation of hESCs, including silencing of pluripotence-associated hsa-miR-302 family and a drastic expression increase of neural-driving Hox miRNA hsa-miR-10 family upon RA exposure [8] (FIGS. 6-10). This invention opens a new dimension of small molecule-mediated direct control and modulation of hESC pluripotent fate when deriving an unlimited supply of clinically-relevant lineages for regenerative therapies. This invention enables well-controlled efficient derivation of a large supply of robust human stem/progenitor/precursor cells and specialized mature functional cells from pluripotent hESCs that can be used in the clinical setting for tissue and organ regeneration and repair.

To address whether this novel human neuronal progenitors hESC-I hNuPs could be safely engrafted in the brain and could migrate and retain their neurogenic ability in vivo, hESC-I hNuPs were transplanted into the cerebral ventricles of newborn mice. This route allows excellent access to the subventricular zone (SVZ), a secondary germinal zone from which cells widely migrate and respond to appropriate regional developmental cues. After at least 3 months post-grafting, the mice were sacrificed and processed for histological and immunocytochemical (ICC) analysis. Transplanted hESC-I hNuPs engrafted and migrated widely and yielded well-dispersed and well-integrated human neurons exclusively at a high prevalence, including nurr1-positve DA neurons, within neurogenic regions of the brain (FIG. 11), demonstrating their potential for neuron regeneration/replacement cell therapy [9, 10]. No graft overgrowth, formation of teratomas or neoplasms, or appearance of non-neuronal cell types was observed following engraftment.

The invention enables developing human-pluripotent-stem-cell-derived therapeutic products and supplies, including patient-specific human stem/precursor/progenitor cells, disease-targeted specialized human cells, and cell- or bio-engineered human tissues and replacement organs that can be used in the clinical setting for repair/reconstruction/replacement of the damaged human body structure and circuitry, as well as developing technologies and methods of human tissue and organ regeneration, including high throughput and high content assays, analytical and manipulation tools, therapeutic strategies, and tissue and organ engineering approaches.

The methods, compositions, tools, and products described herein are presently representative of preferred embodiments and are exemplary and are not intended as limitations on the scope of the invention. Changes therein and other uses will occur to those skilled in the art which are encompassed within the spirit of the invention and are defined by the scope of the disclosure. Accordingly, it will be apparent to one skilled in the art that varying substitutions and modifications may be made to the invention disclosed herein without departing from the scope and spirit of the invention.

The terms and expressions that have been employed are used as terms of description and not of limitation, and there is no intent in the use of such terms and expressions to exclude any now-existing or later-developed equivalent of the features shown and described or portions thereof, but it is recognized that various modifications are possible within the scope of the invention as claimed. Thus, it will be understood that although the present invention has been specifically disclosed by preferred embodiments and optional features, modification and/or variation of the disclosed elements may be resorted to by those skilled in the art, and that such modifications and variations are within the scope of the invention as claimed.

CONCLUSION

The present invention provides the techniques for high efficient direct conversion of pluripotent human embryonic stem cells (hESCs) uniformly into neuronal or cardiac lineage-specific functional cell products by small molecule induction for CNS or myocardium regeneration. The claims of the invention are provided a method of generating a neuronal or cardiomyocyte lineage-specific functional cell product from pluripotent human embryonic stem cells by promoting neural or cardiac lineage-specific differentiation of pluripotent hESCs using small molecule induction. A distinctly claiming subject matter of the invention is provided a method of using retinoic acid (RA) to induce the specification of neuroectoderm direct from the pluripotent state of hESCs in a defined culture platform and trigger the progression to human neuronal progenitors and human neurons in high efficiency, purity, and neuronal lineage specificity. Another distinctly claiming subject matter of the invention is provided a method of using nicotinamide (NAM) to induce the specification of cardiomesoderm direct from the pluripotent state of hESCs in a defined culture platform and trigger the progression to cardiac precursors and beating cardiomyocytes in high efficiency, purity, and cardiac lineage specificity.

INDUSTRIAL APPLICABILITY

The invention provides human CNS and heart-related cells useful for transplantation, research, drug development, tissue and organ engineering, tissue and organ regeneration, scale-up production, cell-based therapy, and other purposes.

What is claimed as the invention is:

1. A method of directly differentiating human embyronic stem (hES) cells into cells of a neuronal lineage comprising:
   (i) providing a culture of hES cells in a defined medium comprising bFGF, insulin, ascorbic acid, and activin A, wherein said defined medium is free of serum, free of feeder cells, and free of feeder cell conditioned medium; and
   (ii) adding retinoic acid to the culture, wherein the hES cells are cultured in the presence of retinoic acid for a period of time sufficient to cause Nurr-1 to translocate to the nucleus and cause the hES cells to directly differentiate into cells of neuronal lineage, wherein said hES cells differentiate into a population of neuronal lineage cells comprising at least 90% neuroectodermal cells that are positive for at least 4 markers selected from the group consisting of Nurr-1, HNK-1, AP2, TrkC, beta-III-tubulin, SSEA-1, microRNA has-miR-10, acetylated histones, Brg-1 and hSNF2H.

2. The method according to claim 1, wherein said defined medium comprises: (a) a basal medium; (b) 20-100 ng/ml of bFGF; (c) 10-30 µg/ml of insulin; (d) 40-60 µg/ml ascorbic acid; and (e) 20-100 ng/ml activin-A.

3. The method according to claim 1, wherein at least 70% of the hES cells of (i) are positive for at least 4 markers selected from the group consisting of alkaline phosphatase, Oct-4, SSEA-4, Tra-1-60, Tra-1-81, acetylated histones, Brg-1 and hSNF2H and micro RNA has-mir-302.

4. The method according to claim 1, wherein the cells of neuronal lineage are selected from the group consisting of neuroectodermal cells, neuronal progenitor cells, neuronal cells, pigmented neuronal cells, dopaminergic neurons, and motor neurons.

5. The method according to claim 1, wherein the RA is selected from the group consisting of all-trans-retinoic acid, 9-cis retinoic acid, and analogues of retinoic acid.

6. The method according to claim 1, wherein said neuroectodermal cells are negative for at least 4 markers selected from the group consisting of Oct-4, SSEA-4, Tra-1-60, Tra-1-81, microRNA hsa-miR-302, Nestin, Sox-2, Musashi, Pdx1, AFP, Nkx2.5, MBP, and GFAP.

7. The method according to claim 1, further comprising removing bFGF from the culture of step (ii) once neuroectodermal cells are obtained, wherein said neuroectodermal cells further differentiate into a population of cell comprising at least 90% of neuronal cells positive for at least 3 markers selected from the group consisting of Nurr-1, beta-III Tubulin, Map-2, NeuN, 70 KDa NF, 160 KDa NF, microRNA hsa-let-7, Micro RNA hsa-miR-143, Micro RNA hsa-miR-124, and Micro RNA hsa-miR-210.

8. The method according to claim 7, wherein said neuronal cells are negative for at least 4 markers selected from the group consisting of Oct-4, SSEA-4, Tra-1-60, Tra-1-81, microRNA hsa-miR-302, Nestin, Sox-2, Musashi, Pdx1, AFP, Nkx2.5, MBP, and GFAP.

9. The method according to claim 7, wherein said neuronal cells comprise dopaminergic neurons and motor neurons that are positive for at least one marker selected form the group consisting of tyrosine hydroxylase, Lmx1, Msx1, Pitx3, HB9, Lim3, and Isl1.

* * * * *